US00PP35520P2

(12) United States Plant Patent
Berry

(10) Patent No.: US PP35,520 P2
(45) Date of Patent: Dec. 5, 2023

(54) ***HIBISCUS* PLANT NAMED 'JBG 19110'**

(50) Latin Name: *Hibiscus rosa-sinensis*
Varietal Denomination: JBG 19110

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/203,237

(22) Filed: May 30, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — The Webb Law Firm

(57) ABSTRACT

A new and distinct *Hibiscus* plant having bright pink with white colored flowers with a prominent eye and plentiful flowers.

2 Drawing Sheets

Botanical Classification: *Hibiscus rosa-sinensis.*
Varietal denomination: 'JBG 19110'.

BACKGROUND OF THE INVENTION

The present invention comprises a new and distinct *Hibiscus* plant having the varietal name 'JBG 19110'. The new variety is the result of a planned breeding program with the purposes of developing *Hibiscus rosa-sinensis* plants that exhibit whitefly and bacterial and fungal leaf spot resistance, propagation and production efficiencies, durable and exotic flowers, and abundant flowering. 'JBG 19110' is the result of a cross conducted in Grand Saline, Texas between *Hibiscus rosa-sinensis* varieties 'AH-60' (female parent, unpatented) and 'MH-05' (male parent, unpatented). The new variety was selected in April of 2018 in Grand Saline, Texas and the first asexual reproduction of the new variety was conducted by semi-hardwood cuttings in September of 2018 in Grand Saline, Texas. 'JBG 19110' has been trial and field tested and has been found to retain its distinctive characteristics and remain true to type through successive propagations. The present invention has not been evaluated under all possible environmental conditions. However, it has been found to thrive in production and adapt well to the environment in Homestead, Florida. The phenotype may vary with variations in environment without a change in the genotype of the plant.

'JBG 19110' is similar to its female parent in having pink and white flower colors, petal ruffling, and foliage size and shape. However, its female parent has mostly white flowers with much less pink present, less visible flower streaking, and a light pink ring around the flower eye that is absent in 'JBG 19110'. 'JBG 19110' is similar to its male parent in having a dark flower eye, upright and vigorous habit, exhibiting streaking in the flower veins, and in flower size. However, 'JBG 19110' differs from its male parent in overall flower color (its male parent is medium-orange in color), being more dense with increased foliage and self-branching, and exhibiting better foliage pest resistance.

When 'JBG 19110' is compared to *Hibiscus rosa-sinensis* variety having the commercial name "Runway Beauty" (unpatented), both varieties have a strong pink flower color, ruffled petals, and similar foliage shape. However, 'JBG 19110' has larger flowers, more vigorous growth, and improved pest and disease resistance.

The following traits distinguish 'JBG 19110' as a new and distinct cultivar from other *Hibiscus* varieties known to the breeder:

1. Bright pink flower color with slightly overlapping blooms:
2. Petal color changes from very dark pink in the winter to light pink with more white edging in the summer;
3. Upright and outward growth habit; and
4. Profuse flowering with multiple flowers open at once.

DESCRIPTION OF THE DRAWINGS

The accompanying photographic images illustrate the new variety at approximately eleven months of age, with the colors being as nearly true as is possible with color illustrations of this type.

DESCRIPTION OF THE PLANT

Figure 1:
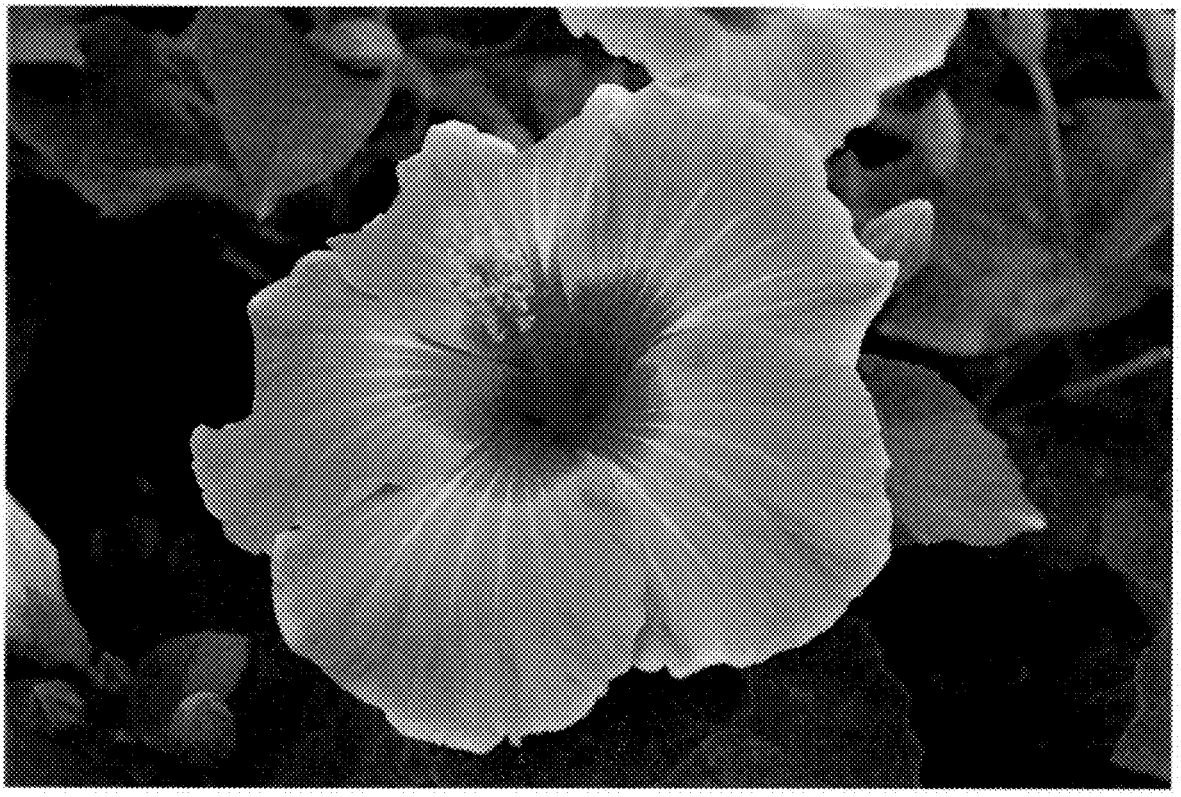
FIG. 1 illustrates a close-up view of a flower of the new variety.
Figure 2:
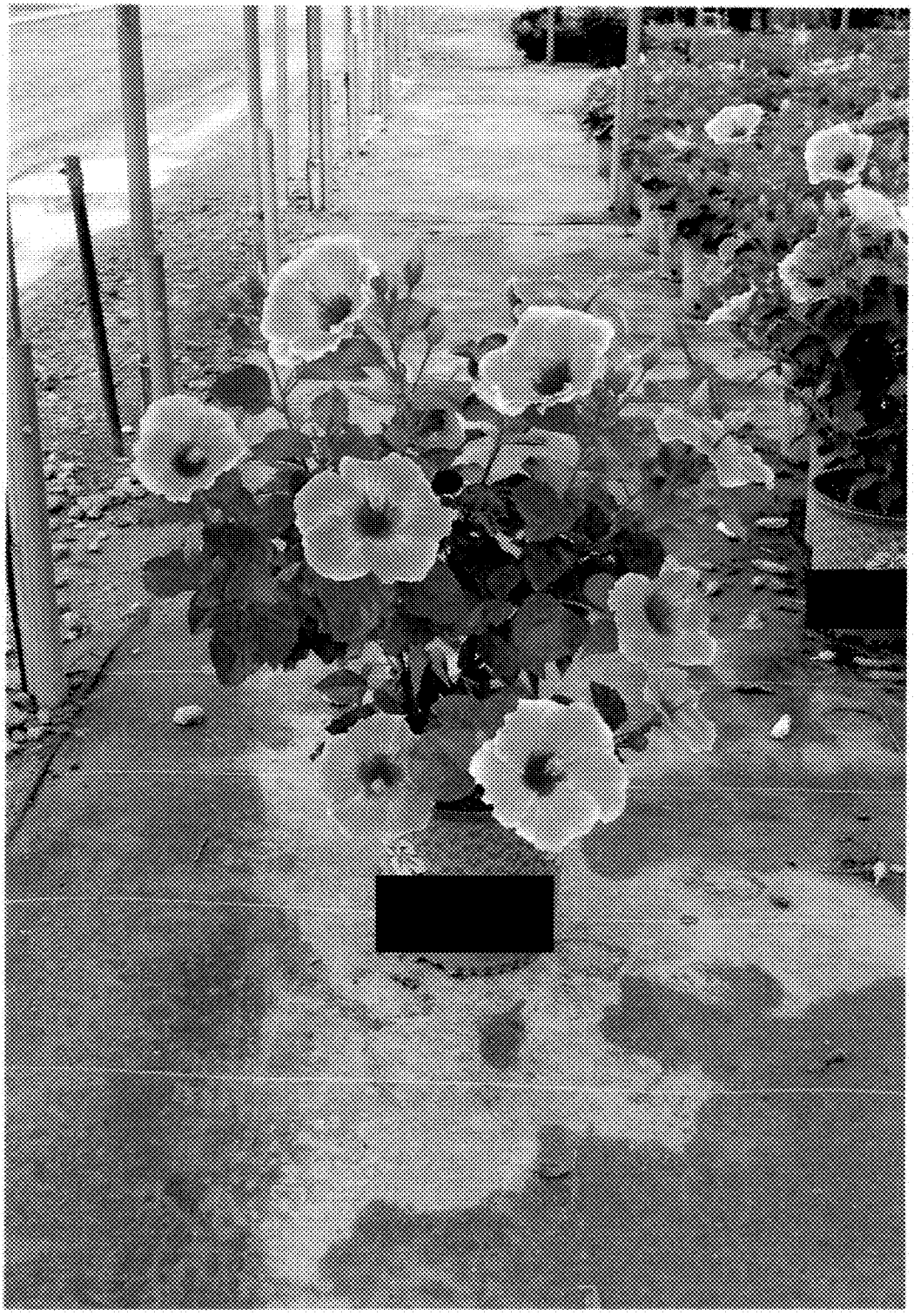
FIG. 2 illustrates an entire plant of the new variety.

The following detailed description sets forth the characteristics of the new variety. The plants were grown in 2 gallon containers in a heated greenhouse with a minimum temperature of approximately 13° C. and about 30% light shade in the summer months. The color readings and measurements were taken indoors under fluorescent lights with natural light from a window nearby on approximately eleven month old plants. Color references are primarily to The 1995 R.H.S. Colour Chart of The Royal Horticultural Society of London, 3$^{rd}$ Edition, except where general color terms are used.

PLANT

Time to initiate roots: About 12 days at an average of 24° C.
Time to develop roots: About 50 days at an average of 21-24° C.
Time to produce a finished flowering plant from a rooted cutting: About 12-16 weeks in a 2 gallon container.
Specific disease/pest resistance: Resistance to whitefly (*Trialeurodes vaporariorum*) and bacterial leaf spot (*Pseudomonas* spp.).
Heat/cold tolerance: Thrives above 13° C., but expires at temperatures of 0° C. and below.
Drought tolerance: Moderate to none.
Plant:
*Type*.—Tropical, ornamental shrub.
*Habit*.—Upright, with high branching that creates a dense shrub.
*Height*.—45.7 cm from the top of the pot to the top of the plant.
*Spread*.—50.8 cm.
*Vigor*.—Moderate to high.
*Rooting*.—Coarse and well-branched.
Stem:
*Number per plant*.—7.
*Length*.—25.4-38.1 cm.
*Width*.—1.0 cm.
*Texture*.—Immature: Slightly coarse with raised bumps. Mature: Very coarse.
*Strength*.—Almost firm.
*Branch number*.—33.
*Internode length*.—3.2-5.7 cm.
*Color*.—Immature: 144B. Mature: 199B.
*Stipules*.—Number per node: 2. Shape: Spinose. Length: 6.0 mm. Width: 1.0 mm. Surface texture: Smooth. Apex: Acute. Base: Linear. Margin: Entire. Color: 143B.
Foliage:
*Arrangement*.—Alternate.
*Size of leaf*.—Length: 9.5 cm. Width: 8.3 cm.
*Shape of leaf* (*generally*).—Ovate.
*Shape of apex*.—Acute.
*Shape of base*.—Cordate.
*Texture*.—Upper surface: Smooth and waxy, with a slight texture from venation. Lower surface: Thin and soft, with prominent texture from venation.
*Margin type*.—Crenate.
*Color*.—Young leaves: Upper surface: 134A. Lower surface: 146A. Mature leaves: Upper surface: 203D. Lower surface: 137B.
*Veins*.—Venation type: Palmate. Color: Upper surface: 137C. Lower surface: 143A.
*Petiole*.—Length: 2.5 cm. Diameter: 3.0 mm. Texture: Mostly smooth. Color: 137B.

FLOWERS

Buds (described at approximately 3 days from opening):
*Shape*.—Elliptical.
*Diameter*.—1.9 cm.
*Length*.—4.6 cm.
Natural flowering season: Year round in Grand Saline, Texas.
Flower type and habit: Single with slightly overlapping petals.
Fragrance: None.
Flowers:
*Number per stem*.—1.
*Overall depth*.—2.5 cm.
*Overall diameter*.—14.6 cm.
*Shape*.—Rotate.
*Lastingness*.—2 days on the plant.
*Petals*.—Number: 5. Arrangement: Simple. Length: 8.9 cm. Width: 7.9 cm. Shape: Ovate. Apex: Obtuse. Base: Acute. Margin: Entire. Texture/appearance: Upper surface: Very smooth, with slight venation texture present. Lower surface: Same as upper surface, but with more venation texture present. Color: When opening: Upper surface: 60D on outside edge; 46B eye color. Lower surface: 186D; 195B on overlapping edge. Fully opened: Upper surface: 156C on outside edge; 54C middle of petal; 44A eye color. Lower surface: 50D primarily; 160C on overlapping edge.
*Calyx*.—Form: Fused. Overall length: 4.1 cm. Overall diameter: 1.9 cm. Sepals/calyx lobes: Number: 5. Shape: Lanceolate. Apex: Acute. Margin: Entire. Texture: Smooth with slightly textured edges. Color: Outer surface: 143B. Inner surface: 139C.
*Epicalyx*.—Length: 14.0 mm. Width: 4.0 mm. Texture: Slightly textured. Color: 137C. Sepal-like bracts: Not present.
*Bracts*.—Not present.
*Peduncle*.—Length: 15.0 mm. Diameter: 4.0 mm. Strength: Firm. Angle: Mostly straight with a slight curve in the center. Texture: Slightly coarse with a strong feeling. Color: 144C.
Reproductive organs:
*Gynoecium*.—Pistils: Number: 1. Length: 8.4 cm. Stigma: Number: 5. Shape: Curved triangle. Length: 3.0 mm. Diameter: 3.0 mm. Color: 32A. Style: Length: 6.7 cm. Width: 4.0 mm. Color: 46A. Ovary: Shape: Oval. Length: 8.0 mm. Width: 6.0 mm. Color: 154C.
*Androecium*.—Stamens: Number: 90. Position: Below the stigma on the style. Anther: Shape: U-shaped. Diameter: 1.0 mm. Color: 18A. Filament: Length: 5.0 mm. Width: 1.0 mm. Color: 14D. Pollen: Color: 14A. Amount (generally): Moderate.

SEEDS

Seeds: None produced.

I claim:

1. A new and distinct variety of *Hibiscus* plant named 'JBG 19110', substantially as illustrated and described herein.

* * * * *